US012636484B2

(12) United States Patent
Bhargava et al.

(10) Patent No.: US 12,636,484 B2
(45) Date of Patent: May 26, 2026

(54) DISINFECTING CAP FOR MALE AND FEMALE CONNECTORS INCLUDING DEFORMABLE HOUSING

(71) Applicant: Becton, Dickinson and Company, Franklin Lakes, NJ (US)

(72) Inventors: Divik Bhargava, Meerut (IN); Shreyasi Dutta, Bangalore (IN); Reddy Jairam Satwik, Visakhapatnam (IN); Atharva Shetye, Kolhapur (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 603 days.

(21) Appl. No.: 18/100,285

(22) Filed: Jan. 23, 2023

(65) Prior Publication Data

US 2024/0245899 A1     Jul. 25, 2024

(51) Int. Cl.
| | |
|---|---|
| *A61L 2/00* | (2006.01) |
| *A61L 2/18* | (2006.01) |
| *A61M 39/16* | (2006.01) |
| *A61M 39/20* | (2006.01) |
| *A61L 103/05* | (2026.01) |

(52) U.S. Cl.
CPC ............. *A61M 39/165* (2013.01); *A61L 2/18* (2013.01); *A61M 39/20* (2013.01); *A61L 2103/05* (2026.01)

(58) Field of Classification Search
CPC ...... A61M 39/10; A61M 39/20; A61M 39/16; A61L 2/18; A61L 31/00; A61L 2202/24
USPC ............................. 422/28, 32, 292, 297, 300
See application file for complete search history.

(56) References Cited

U.S. PATENT DOCUMENTS

| | | | |
|---|---|---|---|
| 8,671,496 | B2 | 3/2014 | Vaillancourt et al. |
| 8,696,820 | B2 | 4/2014 | Vaillancourt et al. |
| 8,740,864 | B2 | 6/2014 | Hoang et al. |
| 9,039,989 | B2 | 5/2015 | Liu et al. |
| 9,283,369 | B2 | 3/2016 | Ma et al. |
| 9,399,125 | B2 | 7/2016 | Burkholz |
| 9,480,833 | B2 | 11/2016 | Hoang et al. |
| D834,187 | S | 11/2018 | Ryan |
| 10,376,686 | B2 | 8/2019 | Burkholz et al. |
| 10,413,716 | B2 | 9/2019 | Sathe |

(Continued)

FOREIGN PATENT DOCUMENTS

| | | |
|---|---|---|
| CA | 2778635 A1 | 5/2011 |
| WO | 2023102043 A1 | 6/2023 |

*Primary Examiner* — Monzer R Chorbaji
(74) *Attorney, Agent, or Firm* — Servilla Whitney LLC

(57)     ABSTRACT

A cap configured to engage a first connector and a second connector of different types includes a housing having a first end, an open second end, a sidewall extending therebetween, and a radially extending flange extending outward from the sidewall or open second end. The cap also includes an absorbent member disposed in the housing configured to contain a cleaning solution for cleaning and/or disinfecting portions of the first connector or the second connector engaged to the cap. The housing is configured to move between a first position, in which the housing is configured to engage the first connector, and a second position, in which the housing is configured to engage the second connector, by folding over the sidewall of the housing such that, in the second position, the flange surrounds a portion of the sidewall between the first end and the second end of the housing.

20 Claims, 13 Drawing Sheets

(56) References Cited

U.S. PATENT DOCUMENTS

| | | |
|---|---|---|
| 10,871,246 B2 | 12/2020 | Marici et al. |
| 11,083,883 B2 | 8/2021 | Ryan et al. |
| 11,273,298 B2 | 3/2022 | Erekovcanski et al. |
| 11,344,715 B2 | 5/2022 | Erekovcanski et al. |
| 11,389,636 B2 | 7/2022 | Coyle |
| 2010/0172794 A1 | 7/2010 | Ferlic et al. |
| 2012/0302968 A1 | 11/2012 | Tennican |
| 2012/0302997 A1 | 11/2012 | Gardner et al. |
| 2013/0035667 A1 | 2/2013 | Anderson et al. |
| 2013/0178804 A1 | 7/2013 | Tennican |
| 2013/0197485 A1 | 8/2013 | Gardner et al. |
| 2014/0135739 A1 | 5/2014 | Solomon et al. |
| 2015/0005699 A1 | 1/2015 | Burbank et al. |
| 2015/0086441 A1 | 3/2015 | She et al. |
| 2016/0106968 A1 | 4/2016 | Solomon et al. |
| 2016/0144118 A1 | 5/2016 | Solomon et al. |
| 2016/0310720 A1 | 10/2016 | Solomon et al. |
| 2018/0055962 A1 | 3/2018 | Drmanovic |
| 2018/0064604 A1 | 3/2018 | Drmanovic |
| 2018/0071508 A1 | 3/2018 | Drmanovic |
| 2018/0085568 A1 | 3/2018 | Drmanovic |
| 2018/0200500 A1 | 7/2018 | Ziebol et al. |
| 2018/0214242 A1 | 8/2018 | Davis et al. |
| 2018/0214684 A1 | 8/2018 | Avula et al. |
| 2018/0250194 A1 | 9/2018 | Drmanovic |
| 2018/0256804 A1 | 9/2018 | Burbank et al. |
| 2018/0256880 A1 | 9/2018 | Follman et al. |
| 2018/0256881 A1 | 9/2018 | Hitchcock et al. |
| 2018/0256883 A1 | 9/2018 | Follman et al. |
| 2018/0369562 A1 | 12/2018 | Gardner et al. |
| 2019/0038888 A1 | 2/2019 | Gardner |
| 2019/0099593 A1 | 4/2019 | Avula et al. |
| 2019/0117332 A1 | 4/2019 | Davis et al. |
| 2019/0201681 A1 | 7/2019 | Ziebol et al. |
| 2019/0262525 A1 | 8/2019 | Wyeth et al. |
| 2019/0282795 A1 | 9/2019 | Fangrow |
| 2019/0351212 A1 | 11/2019 | Dudar et al. |
| 2020/0121858 A1 | 4/2020 | Anderson et al. |
| 2020/0139037 A1 | 5/2020 | Ziebol et al. |
| 2020/0155794 A1 | 5/2020 | Ziebol |
| 2020/0197686 A1 | 6/2020 | Anderson et al. |
| 2020/0238070 A1 | 7/2020 | Ryan |
| 2021/0001110 A1 | 1/2021 | Bedoe et al. |
| 2021/0093791 A1 | 4/2021 | Anderson et al. |
| 2021/0275707 A1 | 9/2021 | Jiang et al. |
| 2021/0322749 A1 | 10/2021 | Rothenberg et al. |
| 2021/0322750 A1 | 10/2021 | Harandi et al. |
| 2021/0322751 A1 | 10/2021 | Jiang et al. |
| 2021/0322752 A1 | 10/2021 | Jiang et al. |
| 2022/0040469 A1* | 2/2022 | Coyle .................. A61M 39/10 |

* cited by examiner

DISINFECTING CAP FOR MALE AND FEMALE CONNECTORS INCLUDING DEFORMABLE HOUSING

BACKGROUND OF THE INVENTION

Field of the Invention

The present disclosure relates generally to caps for medical connectors and, in particular, to a medical cap configured to be attached to either a male connector or a female connector for sealing, cleaning, and disinfecting portions of the connector.

Description of Related Art

Vascular access devices (VADs) are commonly used medical devices, which can include intravenous (IV) catheters, such as peripheral catheters or central venous catheters. If not properly maintained or if exposed to a non-sterile environment, the VADs can become contaminated, sealed with blood clots, and/or can spread infection. Further, bacteria and other microorganisms may enter into a patient's vascular system from access hubs, ports, or valves upon connection to the VAD to deliver a fluid or pharmaceutical to a patient. Therefore, each access hub, port, valve, or other connection configured for attachment to a VAD is associated with some risk of transmitting a catheter related bloodstream infection (CRBSI) to a patient.

Many medical facilities implement sterile practices and protocols to ensure that VADs and access hubs or ports are used properly and do not become sealed or infected. These protocols often include sterilizing the access hubs, ports, and VADs, as well as flushing the catheter with a flush solution prior to use. Specifically, VAD standards of practice usually recommend flush procedures be performed after catheter placement, before fluid infusion, and before and after drug administration, blood sampling, transfusions, and/or administration of parenteral nutrition. Standards of practice can also require that access hubs, ports, and valves be capped with disinfection caps when not in use to prevent microbial ingress into the hub, port, or valve and to sterilize areas of the hub, port, or valve that contact the VAD. Disinfection caps are disposable cap devices that contain an amount of cleaning or disinfecting solution for sterilizing portions of the port, hub, and valve.

Access hubs and ports can have a variety of different types of male or female connectors for securing the hub or port to the VAD. Currently, practitioners often carry several types of caps with them so that they can cap different types of hubs and ports, which may all be used for a particular patient. For example, caps for male needleless connectors and female needleless connectors, as well as IV and hemodialysis lines, often use different connector designs and may require different caps. There can be "male disinfecting cap devices" for disinfecting ISO594-2 type of female threaded fluid luer connectors and "female disinfecting cap devices" for disinfecting ISO594-2 type of male threaded fluid luer connectors.

Some examples of universal caps that fit on both male and female connectors are known. For example, U.S. Pat. No. 10,871,246, entitled "Universal Connector or Cap for Male and Female Threaded Fittings," which is incorporated herein by reference in its entirety, discloses a cap including a threaded protrusion that can engage both a male connector and a female connector. However, there is a need for simpler cap designs that can be manufactured inexpensively and efficiently. The universal caps of the present disclosure are configured to attach to both male and female medical connectors in a secure manner sufficient for preventing microbial ingress. Also, the caps disclosed herein are configured to be connected or engaged to connectors through friction and/or interference engagements that do not rely upon threads of the connectors. Accordingly, the universal caps disclosed herein can be used with connectors having a variety of thread patterns, arrangements, and dimensions. Further, the universal caps of the present disclosure are configured to be easy to manufacture in a single-molding process.

SUMMARY OF THE INVENTION

According to an aspect of the present disclosure, a cap configured to engage at least a first connector and a second connector of different types includes a housing having a first end, an open second end, at least one sidewall extending between the first end and the second end, and a radially extending flange extending outward from the sidewall or open second end. The cap also includes an absorbent member disposed in the housing configured to contain a cleaning solution for cleaning and/or disinfecting portions of the first connector or the second connector engaged to the cap. The housing is configured to move between a first position, in which the housing is configured to engage the first connector, and a second position, in which the housing is configured to engage the second connector, by folding over the sidewall of the housing such that, in the second position, the flange surrounds a portion of the sidewall between the first end and the second end of the housing.

According to another aspect of the present disclosure, a method for attaching the previously described cap includes a step of folding over the sidewall of the cap, such that the housing moves from the first position to the second position. The method also includes a step of inserting the second connector into the folded over cap, such that a stem of the second connector is received within a slit extending axially through the absorbent member.

According to another aspect of the present disclosure, a method for attaching the previously described cap to the first connector includes a step of inserting an end of the first connector into the cap, with the housing in the first position, such that a tubular body and/or other threads of the female connector contact the absorbent member.

In accordance with an embodiment of the present invention, a cap is configured to engage at least a first connector and a second connector of different types, the cap having a housing having a first end, an open second end, at least one sidewall extending between the first end and the second end, and a radially extending flange extending outward from the sidewall or open second end; and an absorbent member disposed in the housing configured to contain a cleaning solution for cleaning and/or disinfecting portions of the first connector or the second connector engaged to the cap, wherein the housing is configured to move between a first position, in which the housing is configured to engage the first connector, and a second position, in which the housing is configured to engage the second connector, by folding over the sidewall of the housing such that, in the second position, the flange surrounds a portion of the sidewall between the first end and the second end of the housing.

In accordance with an embodiment of the present invention, the first connector is a female needleless connector and the second connector is a male needleless connector.

In accordance with an embodiment of the present invention, the female needleless connector includes a female luer connector, comprising: a tubular body defining a tapered cavity sized to receive a stem of a male luer connector; a septum over an opening of the tubular body; and an external thread extending radially outward from an outer surface of the tubular body.

In accordance with an embodiment of the present invention, the cap is engaged to the female connector by an interference or friction engagement between an inner surface of the sidewall and the outer surface of the tubular body and/or external thread of the female connector.

In accordance with an embodiment of the present invention, the male needleless connector includes a male luer connector, comprising: a stem comprising a proximal end, a distal end, and a tapered outer surface extending therebetween, the stem defining a fluid channel extending through the stem; an annular shield about the stem connected to the proximal end of the stem; and a thread extending inward from an inner surface of the annular shield.

In accordance with an embodiment of the present invention, the cap is engaged to the male connector by an interference or friction engagement between a portion of the folded over sidewall and an inner surface of the annular shield of the male luer connector.

In accordance with an embodiment of the present invention, the cap is sized to receive male and/or female connectors having different thread configurations and dimensions.

In accordance with an embodiment of the present invention, the cap is sized to receive female connectors having an outer diameter of from about 8.0 mm to about 10.0 mm and threads with a width at a crest of from about 0.3 mm to about 1.0 mm and a width at a root of the crest from about 0.5 mm to 1.2 mm.

In accordance with an embodiment of the present invention, the absorbent member is configured to clean and/or disinfect threaded surfaces of the first connector or the second connector.

In accordance with an embodiment of the present invention, the first end of the housing includes a dome-shaped outer surface and a substantially flat inner surface.

In accordance with an embodiment of the present invention, in the second position, an outer surface of a lower portion of the sidewall faces an outer surface of an upper portion of the sidewall.

In accordance with an embodiment of the present invention, the sidewall includes a notch or groove in the sidewall between the upper portion and the lower portion for facilitating folding over of the sidewall to move the housing from the first position to the second position.

In accordance with an embodiment of the present invention, the housing further includes at least one annular ridge extending radially inward from an inner surface of the distal portion of the sidewall.

In accordance with an embodiment of the present invention, the housing further includes a plurality of annular ridges extending radially inward from an inner surface of the lower portion of the sidewall.

In accordance with an embodiment of the present invention, the annular ridges include O-rings extending from the inner surface of the sidewall.

In accordance with an embodiment of the present invention, a wall thickness of the lower portion of the sidewall is less than a wall thickness of the upper portion of the sidewall.

In accordance with an embodiment of the present invention, an outer diameter of the absorbent member substantially matches an inner diameter of the upper portion of the housing.

In accordance with an embodiment of the present invention, the housing includes a thermoplastic polymer comprising at least one of polyester, polycarbonate, polypropylene, polyethylene, polyethylene terephthalate, or acrylonitrile butadiene styrene.

In accordance with an embodiment of the present invention, the absorbent member includes a thermoplastic elastomer comprising at least one of silicone, polypropylene, polyethylene, or synthetic or natural rubber (e.g., isoprene).

In accordance with an embodiment of the present invention, the absorbent member includes a sponge.

In accordance with an embodiment of the present invention, the absorbent member includes an open cell foam, such as a porous foam comprising a thermoplastic elastomer.

In accordance with an embodiment of the present invention, wherein insertion of the first connector or the second connector into the housing causes the absorbent member to axially compress.

In accordance with an embodiment of the present invention, the axial compression of the absorbent member causes the cleaning solution of the absorbent member to contact threads and surfaces of the first connector or the second connector.

In accordance with an embodiment of the present invention, the absorbent member includes a cylindrical body having an outer diameter that substantially matches a minimum inner diameter of the housing, and a slit extending axially through the cylindrical body.

In accordance with an embodiment of the present invention, the slit extends axially through the body to a distal end of the cylindrical body.

In accordance with an embodiment of the present invention, portions of the tubular body separated by the slit are configured to separate to receive a stem of a male luer connector.

In accordance with an embodiment of the present invention, with the housing in the first position, the absorbent member is enclosed within the housing and is accessible through the second open end of the housing and, with the cap in the second position, a lower portion of the absorbent member protrudes beyond the folded over sidewall of the housing.

In accordance with an embodiment of the present invention, the cap further includes the cleaning solution absorbed by the absorbent member.

In accordance with an embodiment of the present invention, the cleaning solution includes Isopropyl Alcohol (IPA).

In accordance with an embodiment of the present invention, the cleaning solution includes from about 0.5% to about 3.5% chlorhexidine gluconate and about 70% IPA.

In accordance with an embodiment of the present invention, the housing is moved from the first position to the second position by applying a downwardly directed force to the first end of the housing and/or applying an upwardly directed force to a distal surface of the flange.

In accordance with an embodiment of the present invention, the cap further includes a protective cover over the open second end of the housing.

In accordance with an embodiment of the present invention, the protective cover is attached to the housing by heat sealing.

In accordance with an embodiment of the present invention, a method for attaching the cap to the second connector includes folding over the sidewall of the cap, such that the housing moves from the first position to the second position; and inserting the second connector into the folded over cap, such that a stem of the second connector is received within a slit extending axially through the absorbent member.

In accordance with an embodiment of the present invention, the second connector includes a male luer connector having: a stem including a proximal end, a distal end, and a tapered outer surface extending therebetween, the stem defining a fluid channel extending through the stem; an annular shield about the stem connected to the proximal end of the stem; and a thread extending inward from an inner surface of the annular shield.

In accordance with an embodiment of the present invention, when engaged to the cap, the stem of the male luer connector is inserted into the slit of the absorbent member and a surface of the folded over housing contacts the threads of the annular shield forming a friction or interference engagement between the cap and the annular shield.

In accordance with an embodiment of the present invention, an inner diameter defined by the threads of the annular shield is less than a maximum outer diameter of the housing, when the housing is in the second position.

In accordance with an embodiment of the present invention, the method also includes removing a protective cover positioned over the open second end of the housing from the housing prior to inserting the second connector into the housing.

In accordance with an embodiment of the present invention, a method for attaching a cap to the first connector includes inserting an end of the first connector into the cap, with the housing in the first position, such that a tubular body and/or other threads of the female connector contact the absorbent member.

In accordance with an embodiment of the present invention, an outer diameter of a tubular body of the first connector is greater than a maximum inner diameter of the housing.

DESCRIPTION OF THE INVENTION

Figure 1B:
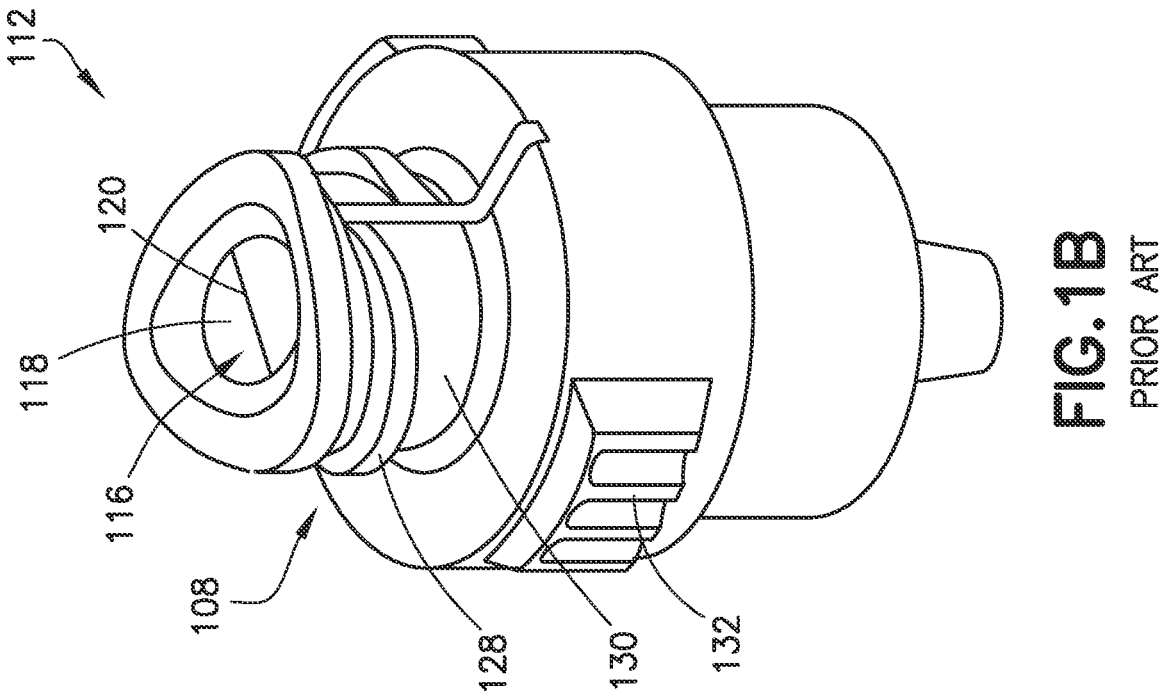
FIG. 1B is an example of a closed female connector including a septum with a slit, as is known in the prior art.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present disclosure is directed to exemplary universal caps 10 configured to be connected to a medical connector 110, 112, such as an access hub, port, or valve for a VAD, by a medical practitioner to prevent the connector, port, or VAD from being contaminated by, for example, microbes, debris, or other contaminants. The medical practitioner can be a clinician or healthcare worker that performs fluid delivery or infusion procedures for patients. In particular, the "healthcare worker" can be a medical professional, such as a medical technician or nurse, trained to perform the medical procedure in accordance with sterile practices and protocols of a medical facility.

In some examples, the caps 10 can be configured to clean or disinfect portions of the connector 110, 112 or port, ensuring that the connector 110, 112 or port remains sterile prior to use. The cap 10 can be configured to remain in place on a connector 110, 112 or port for at least seven days, which is a maximum time of recommended use permitted by many medical facility sterile practice guidelines.

Male and Female Needleless Connectors

The caps 10 of the present disclosure are universal caps configured to engage with or be connected to different sizes, configurations, and/or types of medical connectors 110, 112.

Figure 1A:
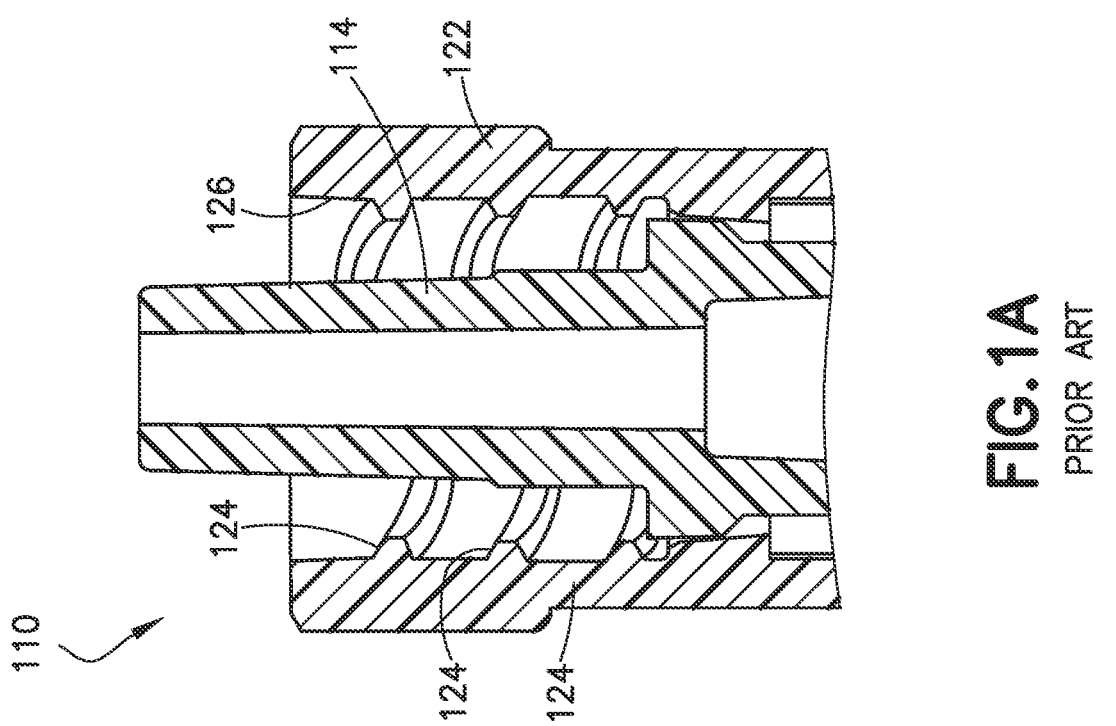
FIG. 1A is a cross-sectional view of an exemplary male connector, as is known in the prior art.

For example, the cap 10 can be configured to engage with or be connected to both a male connector 110 and a female connector 112. As used herein, a "male connector" refers to a connector 110 comprising an elongated member, such as a tubular member or stem 114, configured to be inserted in a tube or opening having an inner diameter that is larger than an outermost diameter of the male connector 110. An exemplary male connector 110 is shown in FIG. 1A. By contrast, a "female connector" refers to a connector 112 comprising an opening or port 116 that is configured to receive an elongated member or tubular member of another object or device in order to connect the object or device to the female connector 112. The female connector 112 can comprise an elongated distal end portion 108 with a cover or septum 118 over the opening 116. An exemplary female connector 112 including a septum 118 with a slit 120 is shown in FIG. 1B.

In some examples, the cap 10 is configured to engage different types of luer connectors, such as both a male luer connector 110 and a female luer connector 112. For example, the cap 10 can be an appropriate size to receive a female luer connector 112 having an outer diameter of about 7.0 mm to about 10.0 mm. The cap 10 can also be sized to receive a male luer connector 110 having an outer diameter of from about 8.0 mm to about 14.0 mm.

As used herein, a "luer connector" refers to a connector that includes a tapered portion (e.g., a luer taper) for creating a friction engagement between a tapered stem 114 or elongated member of a male luer connector 110 and a tapered cavity. For example, the male luer connector 110 can include a tapered stem 114 or elongated member having a tapered outer surface. The female luer connector 112 can include a tapered cavity configured to receive and engage the tapered stem 114 or elongated member to connect the male luer connector 110 to the female luer connector 112.

In some examples, the male connectors 110 and the female connectors 112 can include engaging structures, such as threads, for drawing the connectors 110, 112 to another connector or port. For example, as shown in FIG. 1A, the male luer connector 110 can include an annular shield 122 extending about the tapered stem 114 or elongated member. The annular shield 122 can include threads 124 on an inner surface 126 of the shield 122 configured to engage corresponding threads 128 on an outer surface 130 of the female luer connector 112. As shown in FIG. 1B, the female luer connector 112 includes the threads 128 extending from the outer surface 130 positioned to engage the threads 124 on the inner surface 126 of the annular shield 122 of the male luer connector 110. Twisting the female connector 112 relative to the male connector 110 causes the corresponding threads 124, 128 to engage, which draws the connectors 110, 112 together, such that the tapered stem 114 or elongated member of the male luer connector 110 moves through the opening 116 of the female connector 112. In some examples, the female connector 112 can also include vertical ribs 132 near a proximal end of the female connector 112, which can be used to manipulate the female connector 112 making it easier to twist the female connector 112 relative to another connector or device.

There are numerous commercially available medical devices, such as hubs, ports, and valves, which include different variations of male or female connectors 110, 112, such as male and female luer connectors. As described in further detail herein, the cap 10 of the present disclosure includes a flexible housing, which can bend or deform to create a secure and fluid-tight engagement with a variety of different types and sizes of connectors 110, 112. For example, the cap 10 can be configured to attach to both male and female luer connectors 110, 112, such as male or female Luer-Lok™ connectors by Becton, Dickinson and Company. The cap 10 can also be configured to cover different connector designs including, without limitation, the BD Q-Syte™, BD MaxZero™, BD MaxPlus™, and Smart-Site™ needle free connectors by Becton, Dickinson and Company. The cap 10 can also be configured to be connected to male and/or female connectors by other manufactures including, without limitation, MicroClave® connectors (ICU Medical Inc.) and Ultrasite® connectors (B. Braun Medical Inc.). In other examples, the cap 10 can be configured to be connected to one or more of the following commercially available male connectors: Kendall 2001NP; BD MP5303-C; ICU Med 12664-28; RyMed RYM-5307HPU; B. Braun 470108; Baxter 2C8537; Kawasumi IV-0094; Zyno B2-70071-D; B. Braun 470124; Baxter 2C7462; and Smith's Medical 536035.

Universal Cap for Male and Female Connectors

Figure 2A:
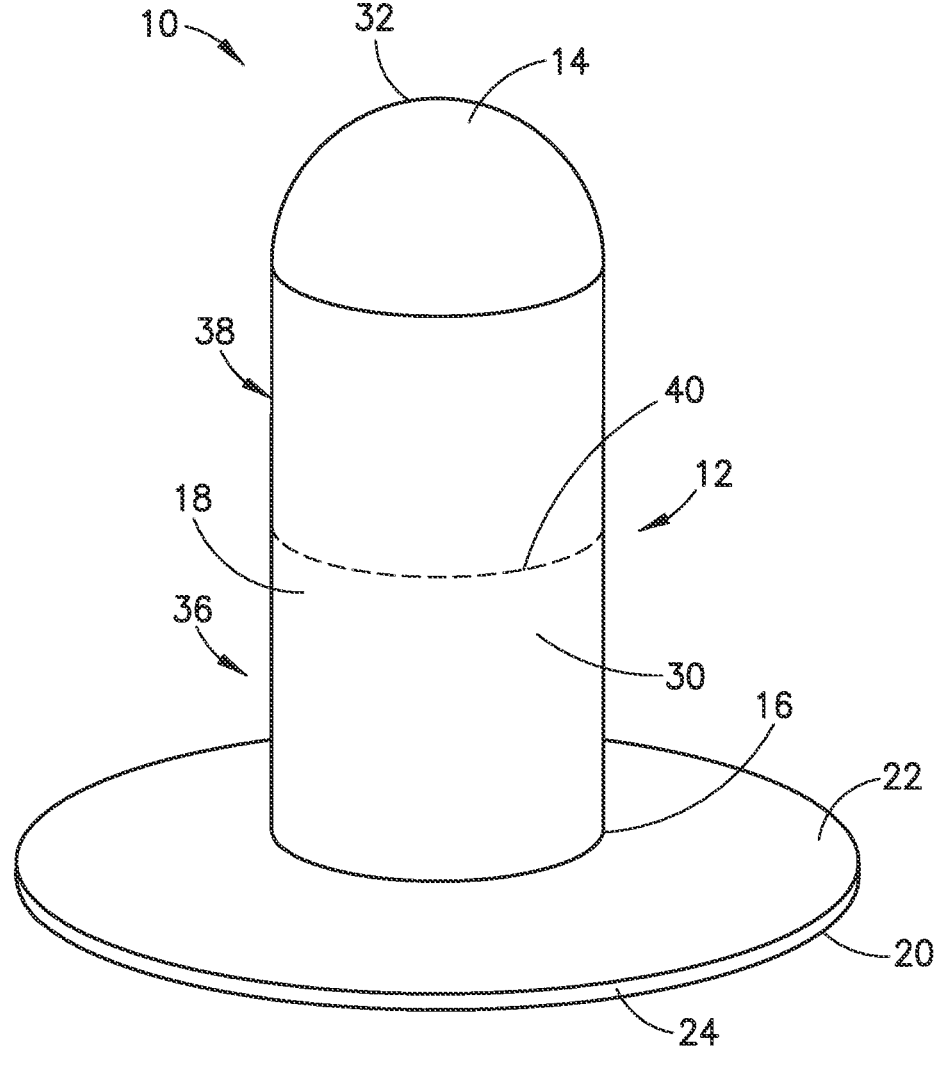
FIG. 2A is a perspective view of a universal cap in an initial position for use with a female connector, according to an aspect of the present disclosure.
Figures 2B, 2C:
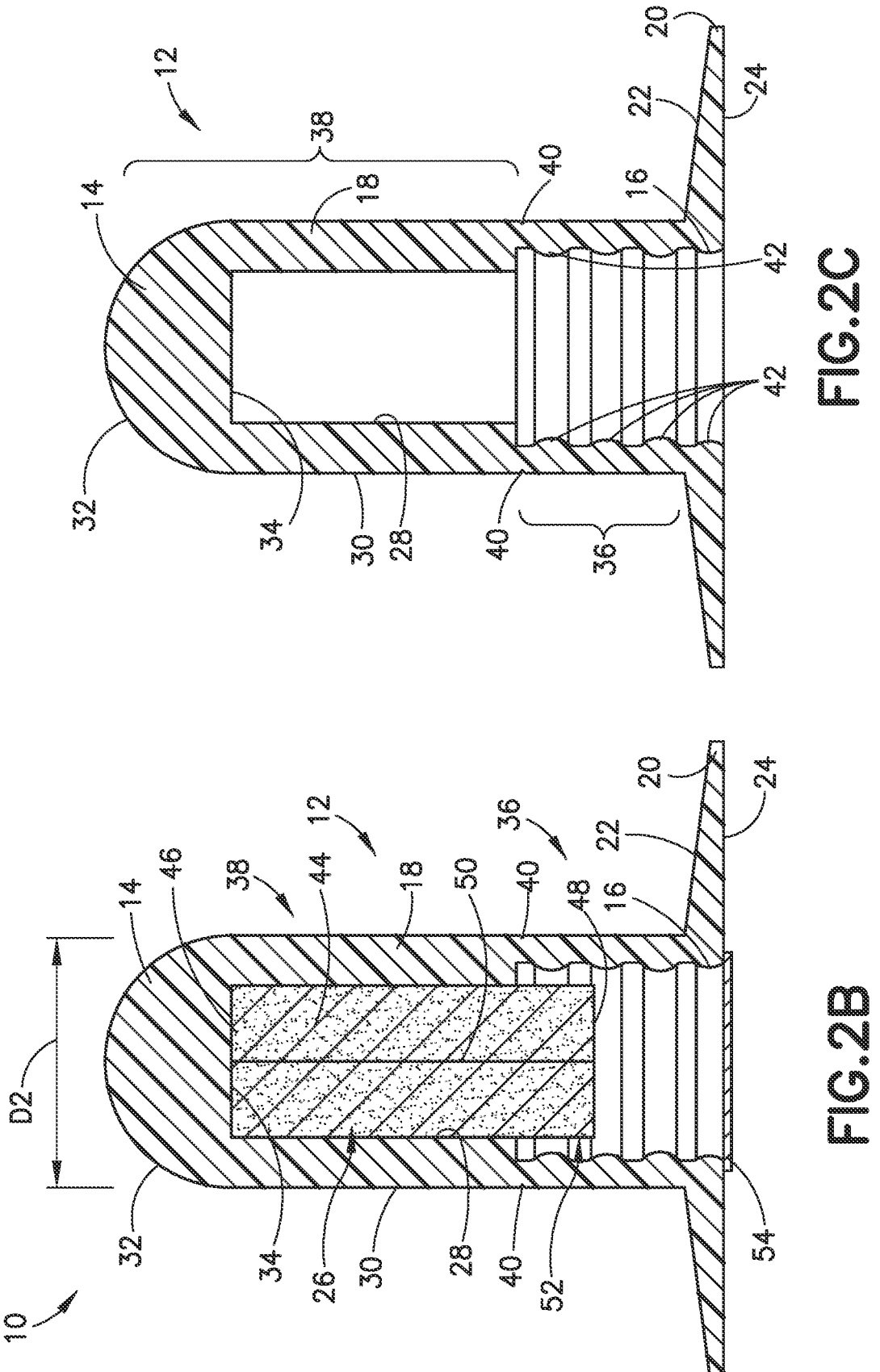
FIG. 2B is a cross-sectional view of the cap of FIG. 2A in the initial position.
FIG. 2C is a cross-sectional view of a housing of the cap of FIG. 2A, according to an aspect of the present disclosure.

FIGS. 2A-2C and 5A-5C illustrate exemplary universal caps 10 configured to engage and/or to be connected to different types of connectors, such as any of the previously described male connectors 110 and female connectors 112. Specifically, FIG. 2A is a perspective view of the cap 10 showing the cap 10 in an initial or extended position, in which the cap 10 is configured to be connected to a female needleless connector 112. FIG. 2B is a cross-sectional view of the cap 10 in the initial position. FIG. 2C is a cross-sectional view of a housing 12 of the cap 10 in the initial position.

Figure 5A:
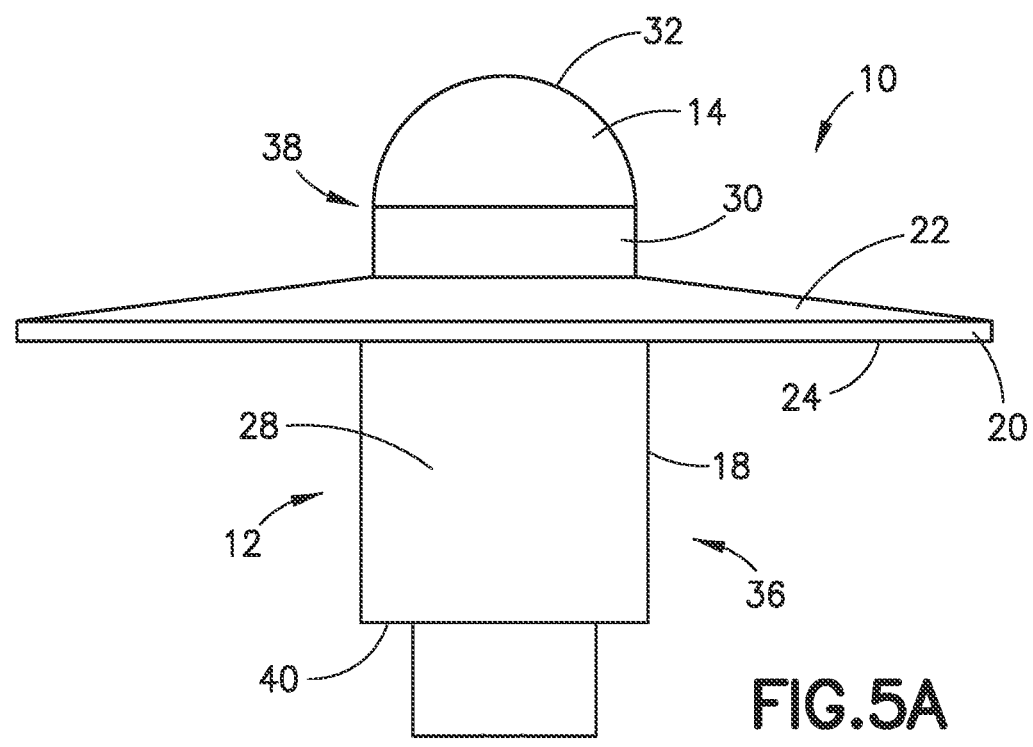
FIG. 5A is a front view of a universal cap in a folded or retracted position for use with a male connector, according to an aspect of the present disclosure.
Figure 5B:
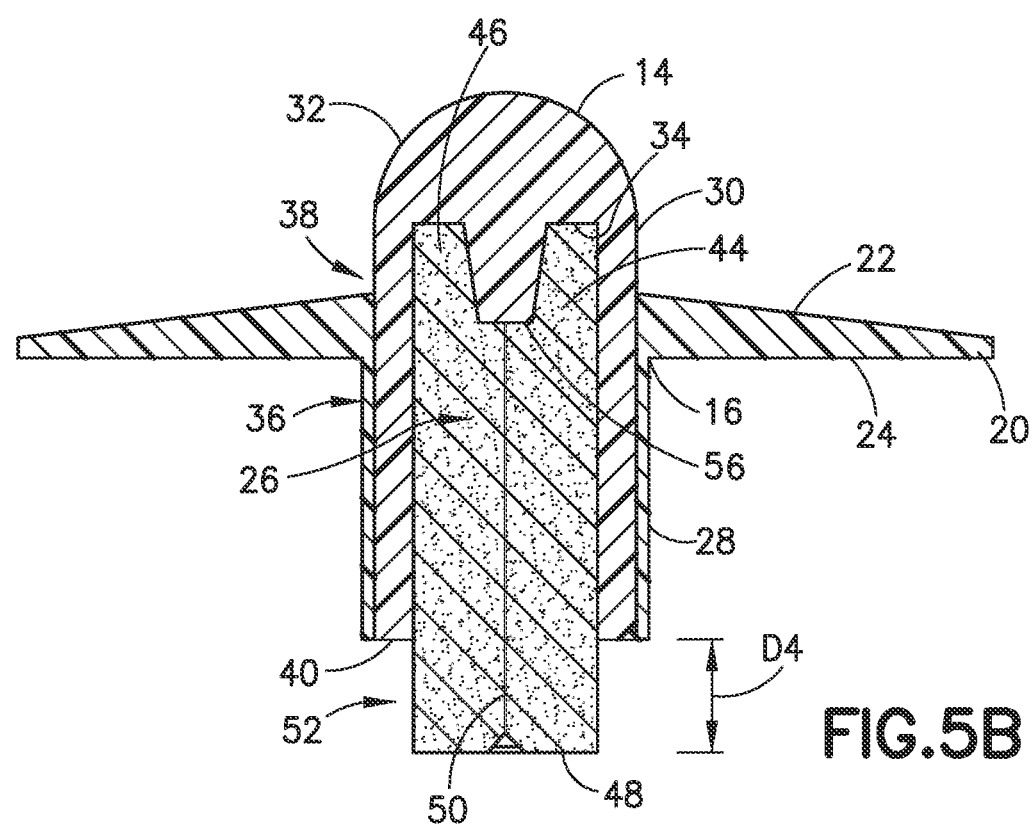
FIG. 5B is a cross-sectional view of the universal cap of FIG. 5A with the cap in the folded or retracted position.
Figure 5C:
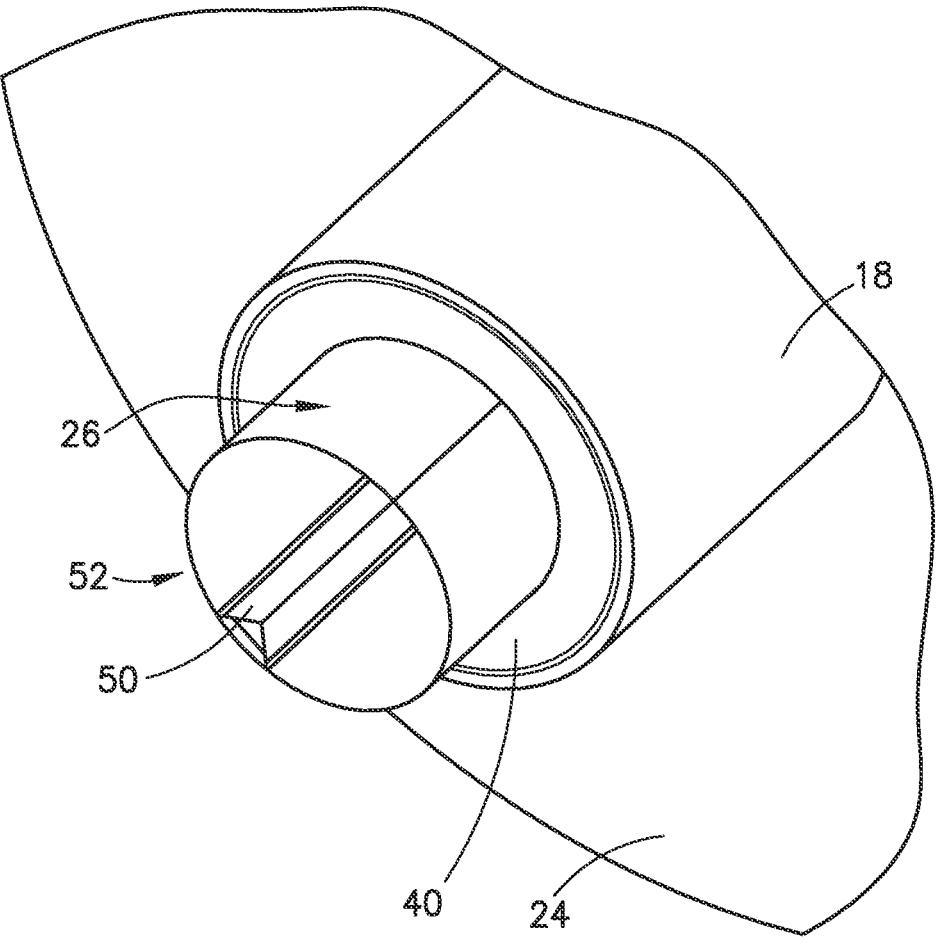
FIG. 5C is an enlarged perspective view of a bottom portion of the cap in the folded or retracted position, according to an aspect of the present disclosure.

As described in further detail herein, caps 10 can also be configured to be moved from the initial position to a second, retracted, or folded position (shown in FIGS. 5A-5C) suitable for connection to a male needleless connector 110. In particular, FIG. 5A is a perspective view of a cap 10 in the folded position. FIG. 5B is a cross-sectional view of the cap 10 in the folded position. FIG. 5C is a perspective view showing a bottom portion of the cap 10 in the folded position.

In some examples, the cap 10 can be provided as a single pre-packaged cap or cap assembly, such as the packaged cap shown in FIG. 2B. Further, as described in further detail herein, the cap 10 includes components, such as sponges, abrasive surfaces, and/or cleaning or disinfecting solutions, for cleaning, scrubbing, and disinfecting portions of male and female connectors 110, 112 inserted into and mounted to the cap 10.

As shown in FIGS. 2A-2C, 5A, and 5B, the cap 10 comprises a housing 12 comprising a first or top end 14, an open second or bottom end 16, and a sidewall 18 extending between the top end 14 and the bottom end 16. The housing 12 also includes a radially extending disk, plate, member, or flange 20 extending radially outward from the open bottom end 16 of the sidewall 18 or housing 12. As shown in the figures, the flange 20 is a generally disk-shaped structure having an upwardly facing surface 22 and a downwardly facing surface 24. The upwardly facing surface 22 can be slightly sloped or angled. By contrast, the downwardly facing surface 24 can be flat allowing the cap 10 to be placed on a flat surface in a vertical orientation. The housing 12 and the flange 20 can be integral portions of a single molded part formed, for example, by a single injection molding process. Generally, the housing 12 and flange 20 are formed from flexible and/or deformable materials to facilitate moving the housing 12 from the initial position to the folded position. For example, the housing 12 and/or flange 20 can be formed from a thermoplastic polymer, such as polyester, polycarbonate, polypropylene, polyethylene, polyethylene tereph-thalate, and/or acrylonitrile butadiene styrene. In some examples, the housing 12 can be formed from a durable material, such as a material having a shore hardness D value of less than or equal to 95 (Shore D). Alternatively, the housing 12 can be formed from a more flexible material, such as a material having a shore hardness A value less than or equal to 130 (Shore A).

As described in further detail herein, the flange 20 can be configured to allow the practitioner to press against the downwardly facing surface 24 of the flange 20, optionally in combination with pressing downward on the top end 14 of the housing 12, to move the housing 12 from the initial position to the folded position. In particular, moving the housing 12 to the folded position causes the sidewall 18 of the housing 12 to flip or fold along a fold line or notch 40, such that, in the folded position shown in FIGS. 5A-5C, the flange 20 surrounds a portion of the sidewall 18 in an intermediate position between the top end 14 and the bottom end 16 of the housing 12. Also, in the folded position, an outer surface 30 of a lower portion 36 of the sidewall 18 faces an outer surface 30 of an upper portion 38 of the sidewall 18.

As used herein, the "lower portion" of the sidewall 18 refers to a portion of the sidewall 18 between the fold line or notch 40 and the bottom end 16 of the housing 12. By contrast, the "upper portion" of the sidewall 18 refers to the portion of the sidewall 18 between the fold line 40 and the top end 14 of the housing 12. In some examples, the fold line 40 can simply be a printed marking showing the practitioner how far to fold over the sidewall 18 in order to use the cap 10 with male needleless connectors 110. In other examples, the fold line 40 can be a physical structure, such as a notch, groove, thin portion, or flexible region provided in or on the sidewall 18 between the upper portion 38 and the lower portion 36 for facilitating folding over of the sidewall 18 to move the housing 12 from the initial position to the folded position. The shape or configuration of the sidewall 18 can also make it easier to fold the sidewall 18 over to move the housing 12 from the initial position to the folded position. For example, a wall thickness of the lower portion 36 of the sidewall 18 can be less than a wall thickness of the upper portion 38 of the sidewall 18, making the lower portion 36 of the sidewall 18 easier to manipulate, bend, and fold when moving the housing 12 from the initial position to the folded position.

While the housing 12 of the cap 10 is generally an elongated tubular structure, the housing 12 can include a variety of structure features for aesthetic or functional purposes. For example, as shown in the figures, the top end 14 of the housing 12 can include a dome-shaped outer surface 32 and a substantially flat inner surface 34.

In some examples, the housing 12 includes interior structures for creating or enhancing an engagement between the connectors 110, 112 and the cap 10. For example, as shown most clearly in FIG. 2C, the cap 10 can include one or more annular ridges, protrusions, surfaces, or members extending radially inward from an inner surface 28 of the sidewall 18. In some examples, the annular ridges or protrusions can be molded structures or members formed on the inner surface 28 of the sidewall 18 during molding. In other examples, the annular ridges can be separate structures that are embedded in or attached to the inner surface 28 of the sidewall 18. For example, the annular ridges can be O-rings 42 positioned around the inner surface 28 of the sidewall 18. In some examples, the O-rings 42 can be inserted into or seated in annular grooves of the inner surface 28 or held in place against the inner surface 28 of the sidewall 18 by adhesives, mechanical fasteners, or other connectors, as are known in the art. In either case, the annular ridges or O-rings 42, if present, are configured to press against the outer surface 130 and/or threads 128 of the female connector 112 for forming a friction or interference engagement with the female connector 112 for securing the cap 10 to the female connector 112. Also, the annular ridges or O-rings 42 can contribute to creating a fluid-tight seal preventing cleaning or disinfecting solution in the cap 10 from leaking from the cap 10 past surfaces of the female connector 112.

The cap 10 further comprises an absorber, absorbent member, or support structure (referred to herein as the absorbent member 26) for cleaning and disinfecting portions of the male and female connectors 110, 112 inserted into the cap 10, such as threaded surfaces (e.g., roots and crests of threads 124, 128) of the connectors 110, 112. In particular, the absorbent member 26 can be configured to clean and disinfect surfaces of the stem 114, as well as the inner surface 126 and threads 124 of the annular shield 122 of the male connector 110. The absorbent member 26 can also be configured to clean and disinfect portions of the distal end portion 108, opening or port 116, and septum 118 of the female connector 112.

As shown in FIG. 2B, the absorbent member 26 can be a substantially tubular or cylindrical structure comprising a top end 46, a bottom end 48, and a cylindrical body 44 extending therebetween. The body 44 can be seated and/or received within a corresponding cylindrical cavity or portion of the housing 12. In some examples, the absorbent member 26 can be held in the interior of the housing 12 by a friction engagement between the absorbent member 26 and the inner surface 28 of a the sidewall 18. In such cases, an outer diameter D1 of the absorbent member 26 can be identical to or substantially match (e.g., be within about 5% or less of) an inner diameter D2 of the upper portion 38 of the sidewall 18 of the housing 12 in order to ensure that there is a robust friction engagement between the sidewall 18 and the absorbent member 26. In other examples, the absorbent member 26 can be held in place within the housing 12 by a conventional adhesive or mechanical fastener, as are known in the art. As shown in FIGS. 2A-2C, when the housing 12 is in the initial position, the absorbent member 26 is entirely enclosed or surrounded by the housing 12 and is accessible through the open bottom end 16 of the housing 12. By contrast, as shown in FIGS. 5A-5C, with the cap 10 in the folded position, a lower portion 52 of the absorbent member 26 protrudes distally beyond the folded over sidewall 18 of the housing 12. For example, the lower portion 52 of the absorbent member 26 can protrude beyond the sidewall 18 by a distance D4 of from about 3 mm to about 6 mm.

In some examples, as shown in FIGS. 2B, 5B, and 5C, the absorbent member 26 includes a cutaway portion, cavity, opening, gap, or slit 50 extending axially through the cylindrical body 44 of the absorbent member 26. In particular, the slit 50 can extend axially though the body 44 from an interior of the body 44 to the bottom end 48 of the body 44. The slit 50 may not extend through the entire body 44 and/or may not extend all the way to the top end 46 of the body 44. The absorbent member 26 including the body 44 separated by the slit 50 is configured to engage with and clean portions of a male connector 110. In particular, the slit 50 can be positioned to receive the stem 114 of the male luer connector 110. Specifically, the stem 114 can be advanced axially through the slit 50, causing portions of the body 44 to separate to receive the stem 114 of the male luer connector 110 forming a friction engagement between an inner surface of the absorbent member 26 and an outer surface of the stem 114.

In some examples, the absorbent member 26 comprises or is formed from an absorbent material capable of absorbing a cleaning or disinfecting solution for cleaning and/or disinfecting portions of the male connector 110 and the female connector 112. Further, the absorbent member 26 can be configured to axially compress as the distal portion of the connector 110, 112 is inserted into the housing 12. The axial compression of the absorbent member 26 can cause the cleaning solution of the absorbent member 26 to flow away from the absorbent member 26 and to contact the threads 124, 128 and other surfaces of the connector 110, 112 for cleaning and disinfecting portions of the connector 110, 112.

In some examples, the absorbent member 26 can comprise a thermoplastic elastomer, such as polypropylene, polyethylene, or synthetic or natural rubber (e.g., isoprene). The absorbent member 26 can also comprise a porous foam (e.g., an open cell foam) or sponge capable of absorbing the cleaning or disinfecting solution, such as a foam or sponge comprising polyurethane. In other examples, the foam material can be a Plastazote® foam, which is an engineered polymer foam by Zotefoams PCL.

In some examples, the absorbent member 26 can be provided (e.g., presoaked) with the cleaning or disinfecting solution. For example, the cleaning or disinfecting solution can be an antimicrobial, anti-fungal, antibacterial, or anti-viral solution that cleans and sterilizes surfaces of the connectors 110, 112. In some examples, the cleaning solution can be isopropyl alcohol (IPA), such as about 70% IPA. In other examples, the cleaning solution can be about 0.5% to about 3.5% chlorhexidine gluconate in combination with about 70% IPA. A chlorohexidine composition may be beneficial because it has a slower evaporation rate than IPA and, therefore, provides a more persistent disinfectant activity after the cap 10 is removed from the connector 110, 112 and before the VAD is connected to the hub, port, or valve.

Figure 7A:
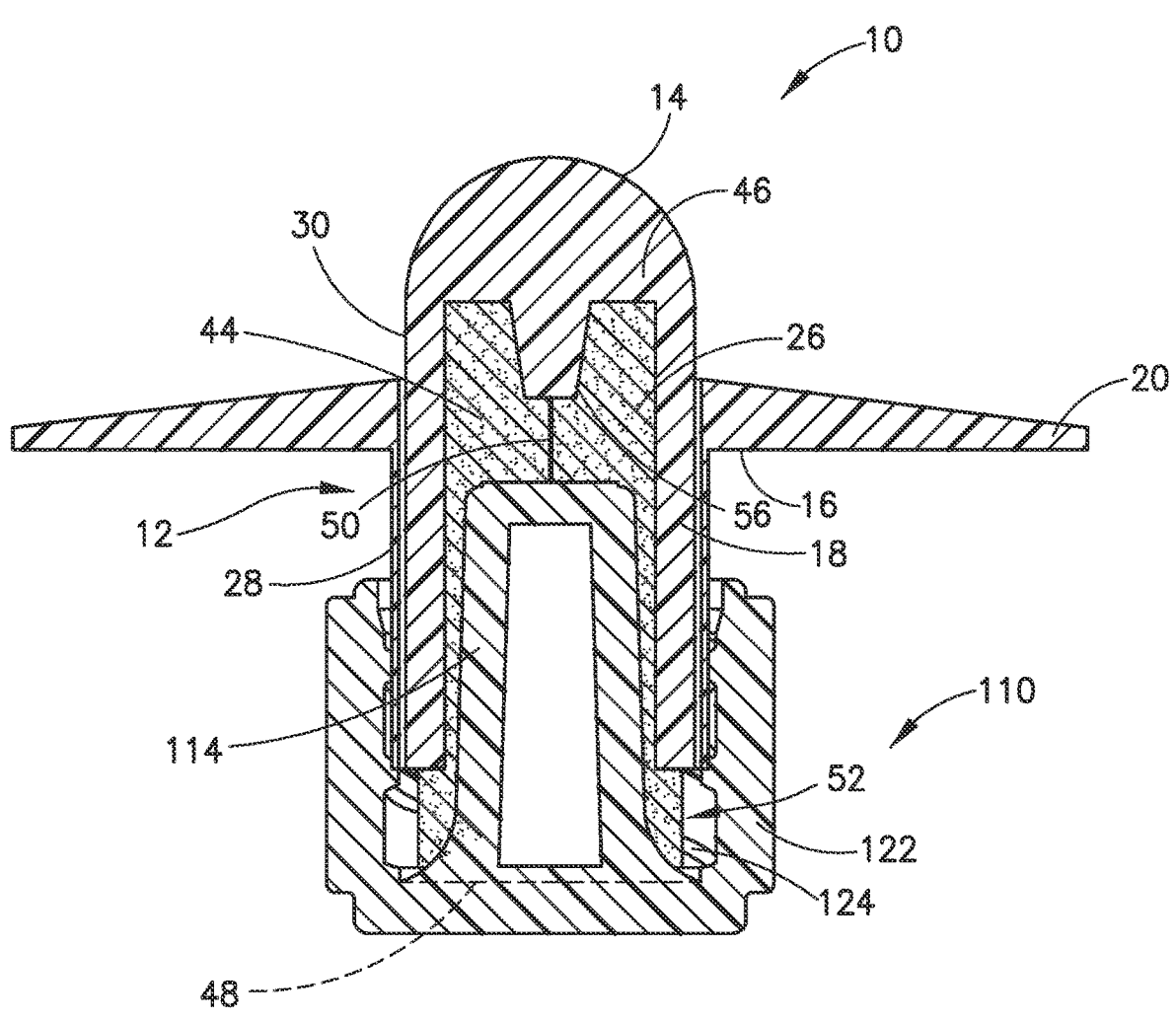
FIG. 7A is a cross-sectional view of the universal cap in the folded or retracted position connected to the male needleless connector of FIG. 6A, according to an aspect of the present disclosure.
Figure 7B:
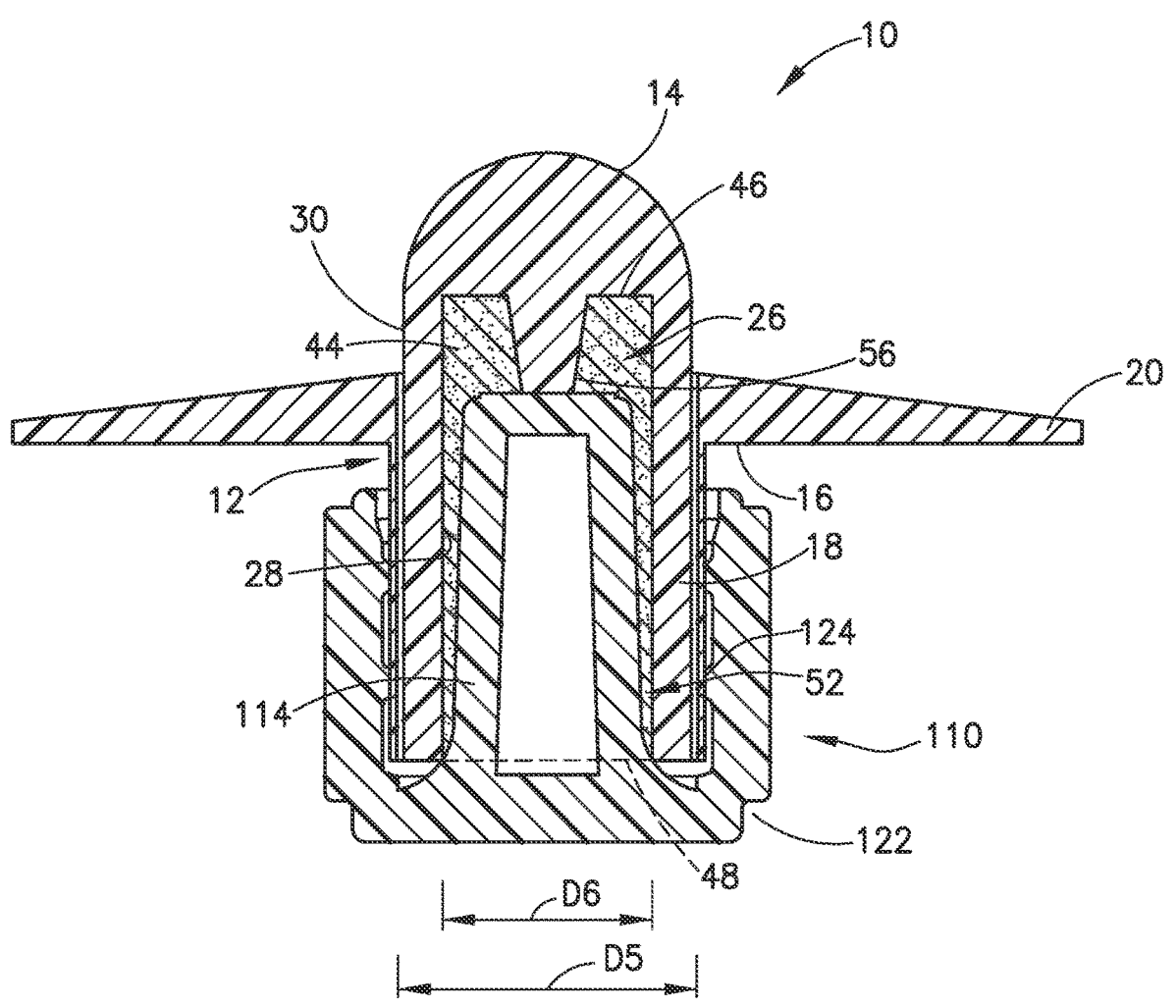
FIG. 7B is another cross-sectional view of the male needleless connector connected to the cap of FIG. 6A, according to an aspect of the present disclosure.

In some examples, as shown most clearly in FIG. 5B, the cap 10 further comprises a protrusion 56 extending inwardly from the flat inner surface 34 of the housing 12 into the absorbent member 26. The protrusion 56 can be a frusto-conical structure including sloped or angled sides and a flat base. The flat base can be sized to cover and/or seal the opening of the stem 114 of the male connector 110, when the male connector 110 is inserted into the cap 10, as shown in FIG. 7B. The protrusion 56 is provided to prevent liquids, such as the cleaning solution, from passing into the fluid passageway or channel of the male connector 110, which could contaminate, for example, a fluid or patient line extending through the male connector 110.

In some examples, the cap 10 further comprises a removable and/or disposable protective cover 54 (shown in FIG. 2B) positioned over the open bottom end 16 of the housing 12. Specifically, as shown in FIG. 2B, the protective cover 54 can extend over the open bottom end 16 and can contact, connect, and/or be adhered to the downwardly facing surface 24 of the flange 20. The protective cover 54 can be provided to protect components and portions of the cap 10, such as the housing 12 and absorbent member 26, during transport and storage to prevent contamination and to prevent the cleaning or disinfecting solution from evaporating prior to use. In some examples, the protective cover 54 can comprise a sheet, such as a polymer film, with adhesive on a first side of the sheet for removably mounting the protective cover 54 to the downwardly facing surface 24 of the flange 20. Alternatively, the protective cover 54 can be removably mounted to the downwardly facing surface 24 of the flange 20 by heat sealing. The protective cover 54 can be formed from a material that is impervious or substantially impervious to air, so that the cleaning or disinfecting solution on the absorbent member 26 does not evaporate or dry-out. Accordingly, the protective cover 54 can increase a shelf life of the cap 10, as well as prevent microbes and other debris from collecting in the cap 10 prior to use.

Figure 6A:
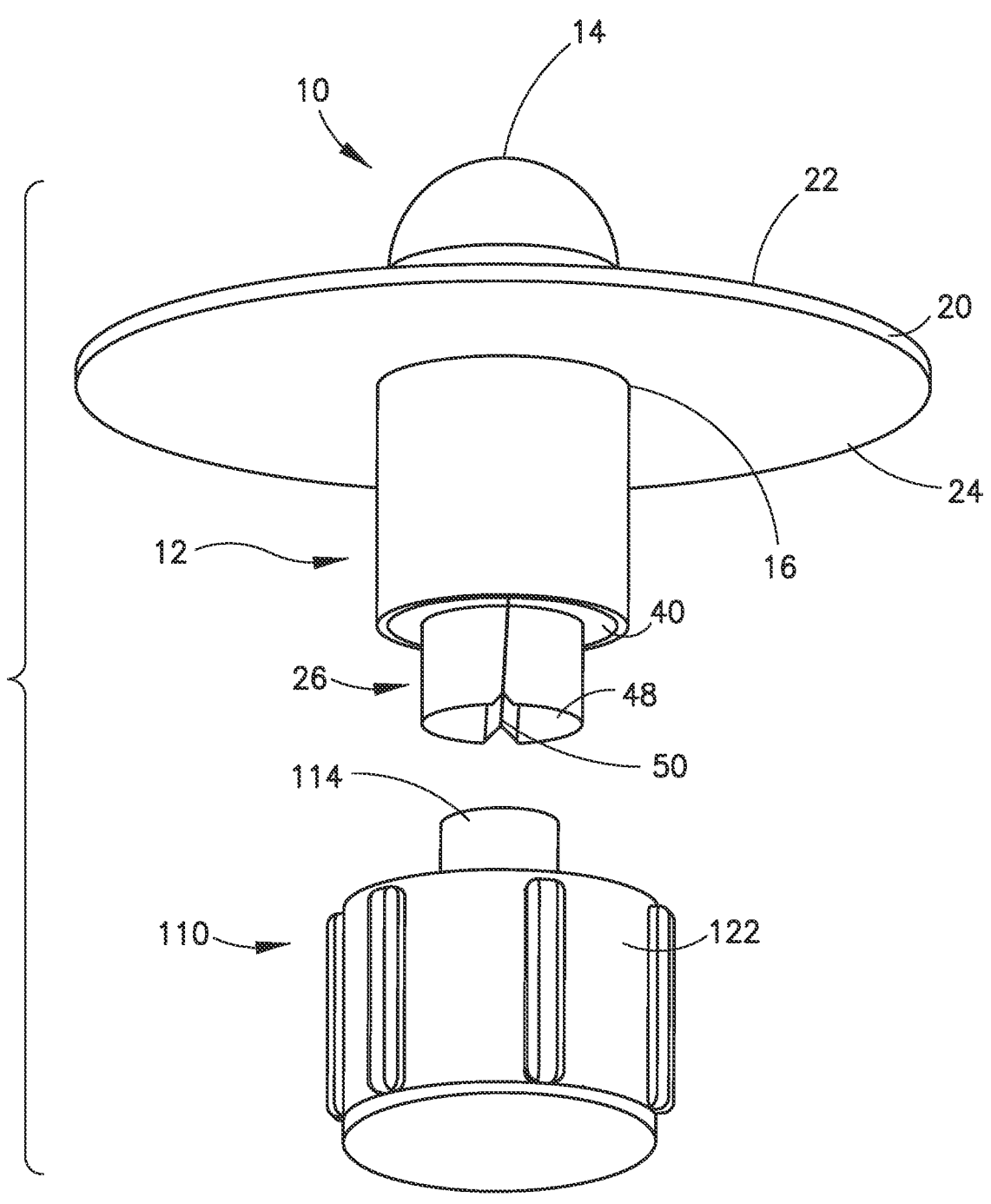
FIG. 6A is a perspective view of the universal cap of FIG. 5A in the folded or retracted position and a male needleless connector prior to inserting the male needleless connector into the cap, according to an aspect of the present disclosure.
Figure 6B:
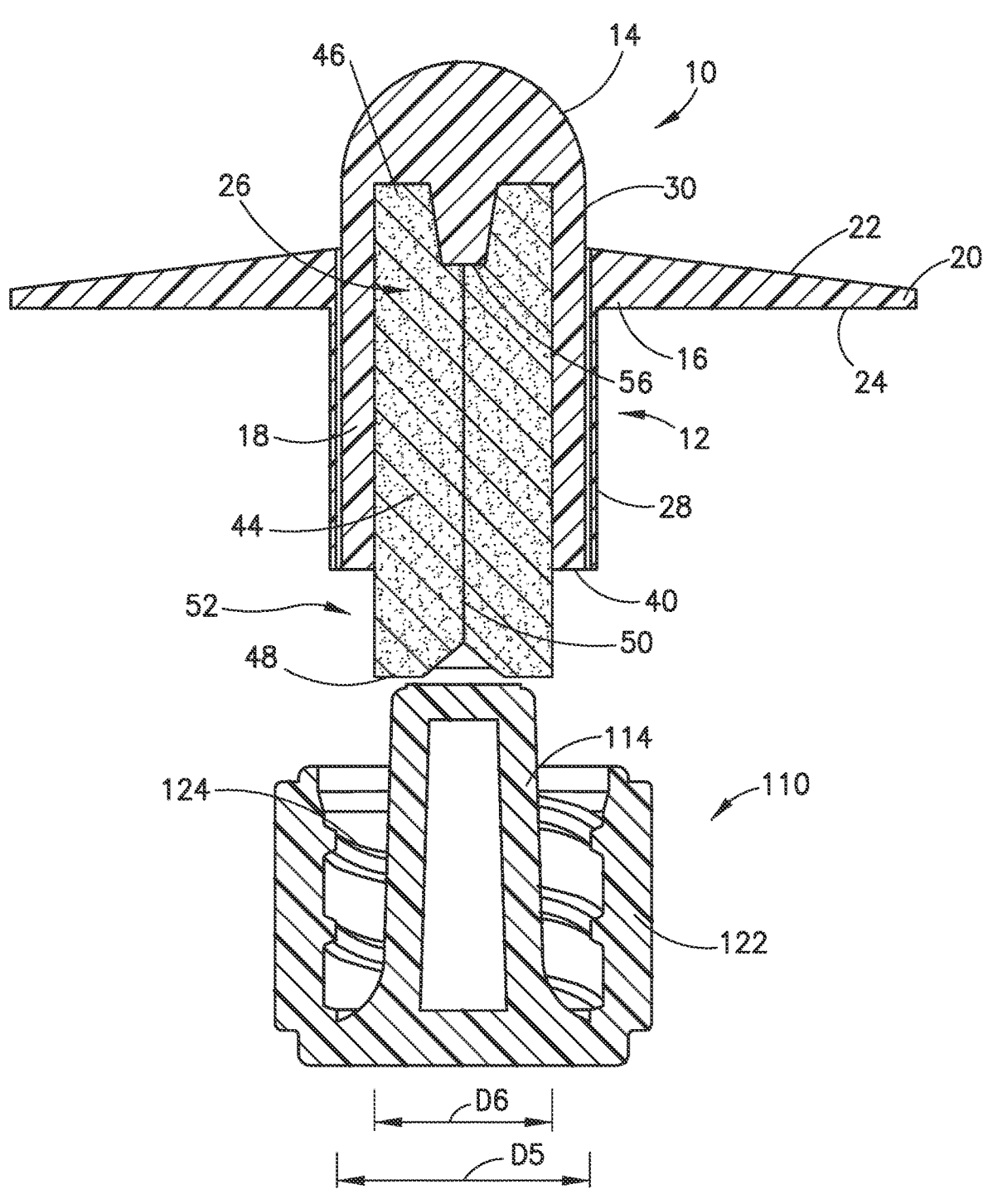
FIG. 6B is a cross-sectional view of the universal cap and the male needleless connector of FIG. 6A.
Figure 6C:
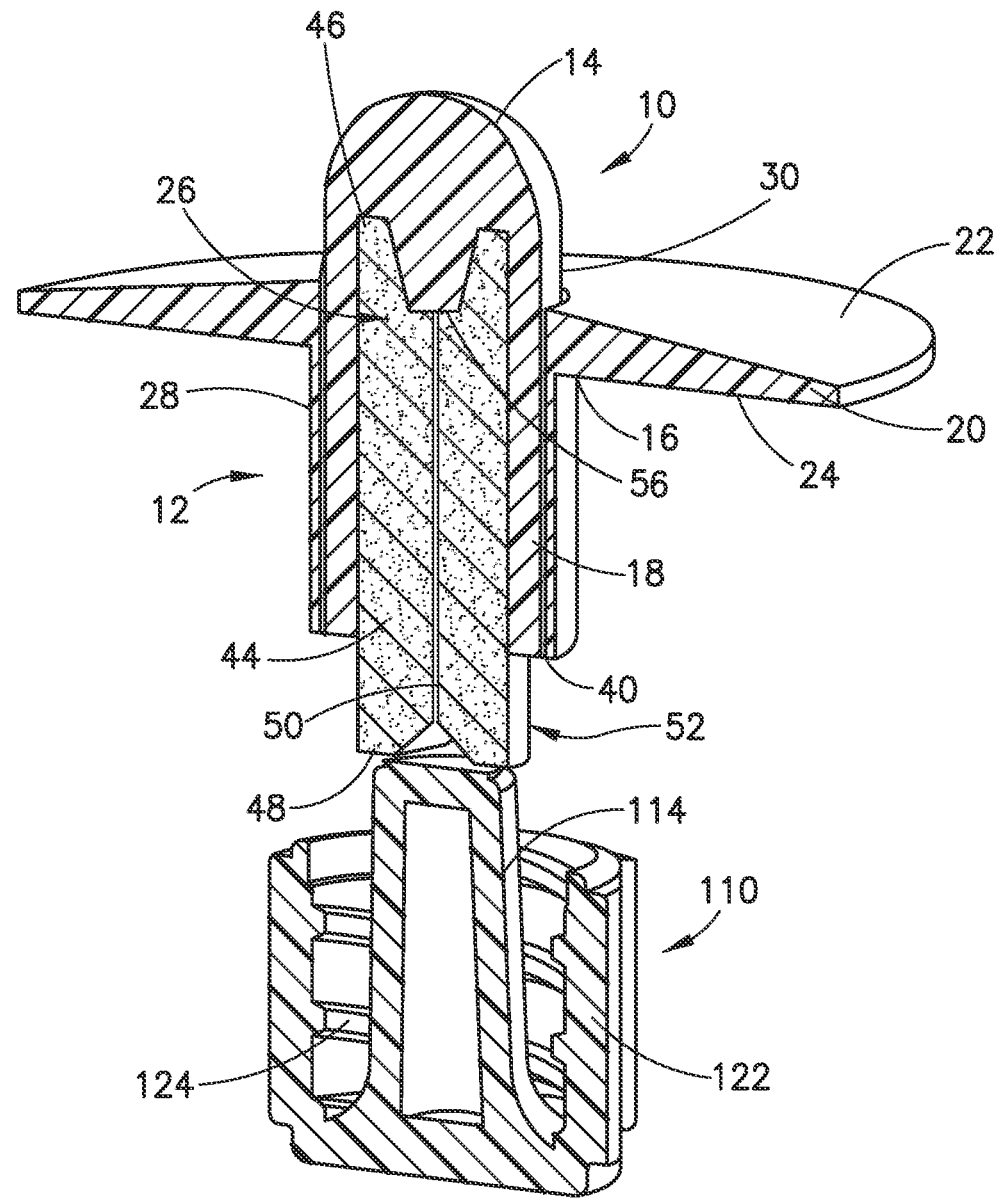
FIG. 6C is a perspective view of a cross-section of the universal cap and the male needleless connector of FIG. 6A.

As previously described, the cap 10 is configured to form a friction and/or interference engagement with female and male connectors 110, 112 of different configurations and types. Accordingly, while portions of the housing 12 can be deformable to account for size differences, the dimensions of the cap 10 are generally selected to ensure that there is a good friction fit between the cap 10 and a connector 110, 112 of an expected, conventional, or common size. For example, the cap 10 is configured to engage to the female connector 112 by an interference or friction engagement between an inner surface 28 of the sidewall 18 and the outer surface 130 of the distal portion 108 of the tubular member 114 and/or external thread 128 of the female connector 112. In order to create the good friction and/or interference engagement, an outer diameter D3 (shown in FIGS. 3A and 3B) of the distal end portion 108 and/or threads 128 of the tubular member 114 of the female connector 112 is greater than a maximum inner diameter D7 (shown in FIG. 3B) of the housing 12. In a similar manner, the cap 10, in the folded position, is configured to engage the male connector 110 by an interference or friction engagement between a portion of the folded over sidewall 18 and an inner surface 126 or threads 124 of the annular shield 122 of the male luer connector 110 as shown, for example, in FIGS. 7A and 7B. In order to create the good friction and/or interference engagement with the male connector 110, a maximum outer diameter D5 (shown in FIGS. 6B and 7B) of the sidewall 18 of the housing 12 can be greater than an inner diameter D6 (shown in FIGS. 6B and 7B) of the threads 124 or inner surface 126 of the annular shield 122 ensuring that the sidewall 18 of the cap 10 is secured within the annular shield 122.

Method for Attaching a Connector to the Cap

Figure 3A:
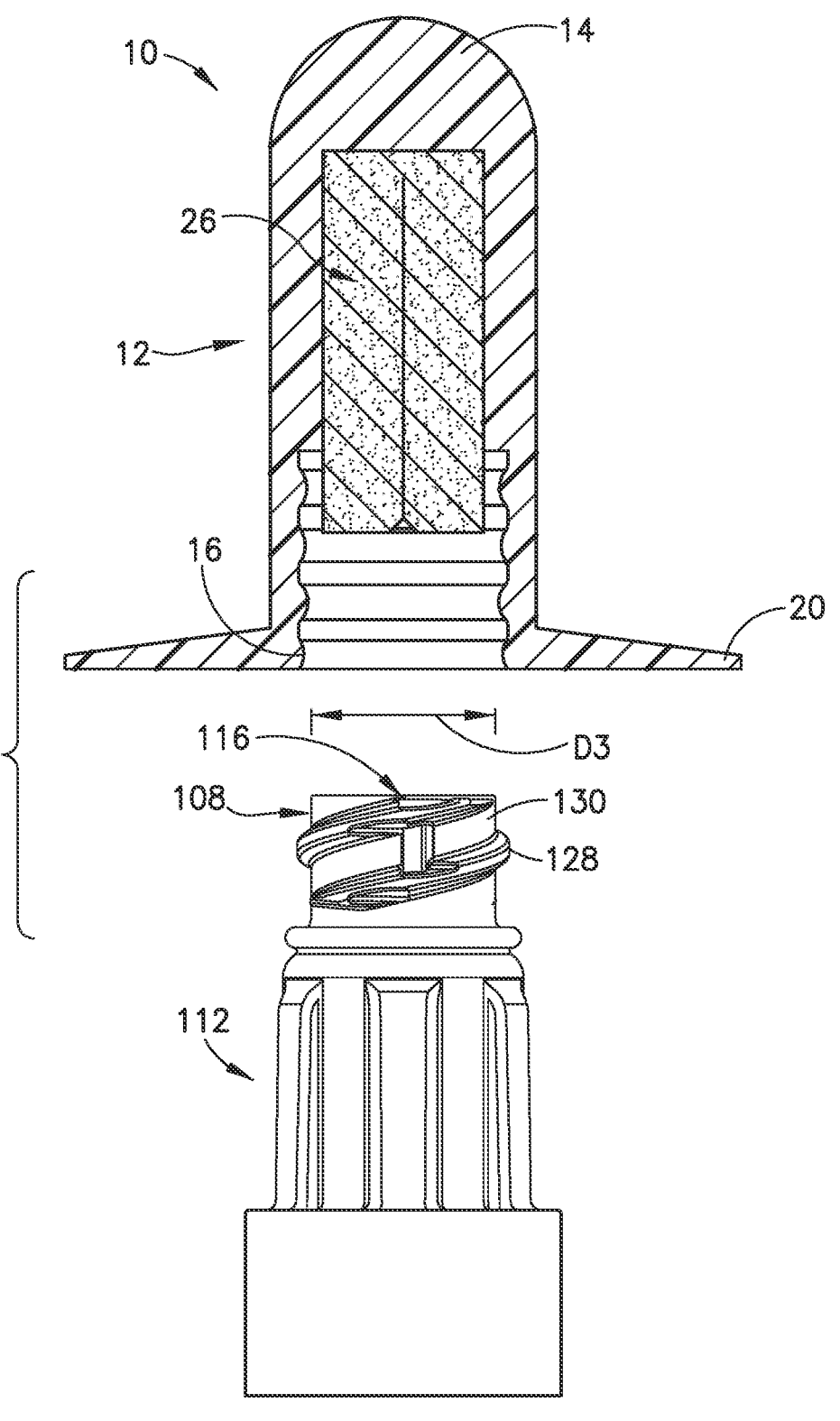
FIG. 3A is a cross-sectional view of the cap of FIG. 2A in the initial position and a female needleless connector, according to an aspect of the present disclosure.
Figure 3B:
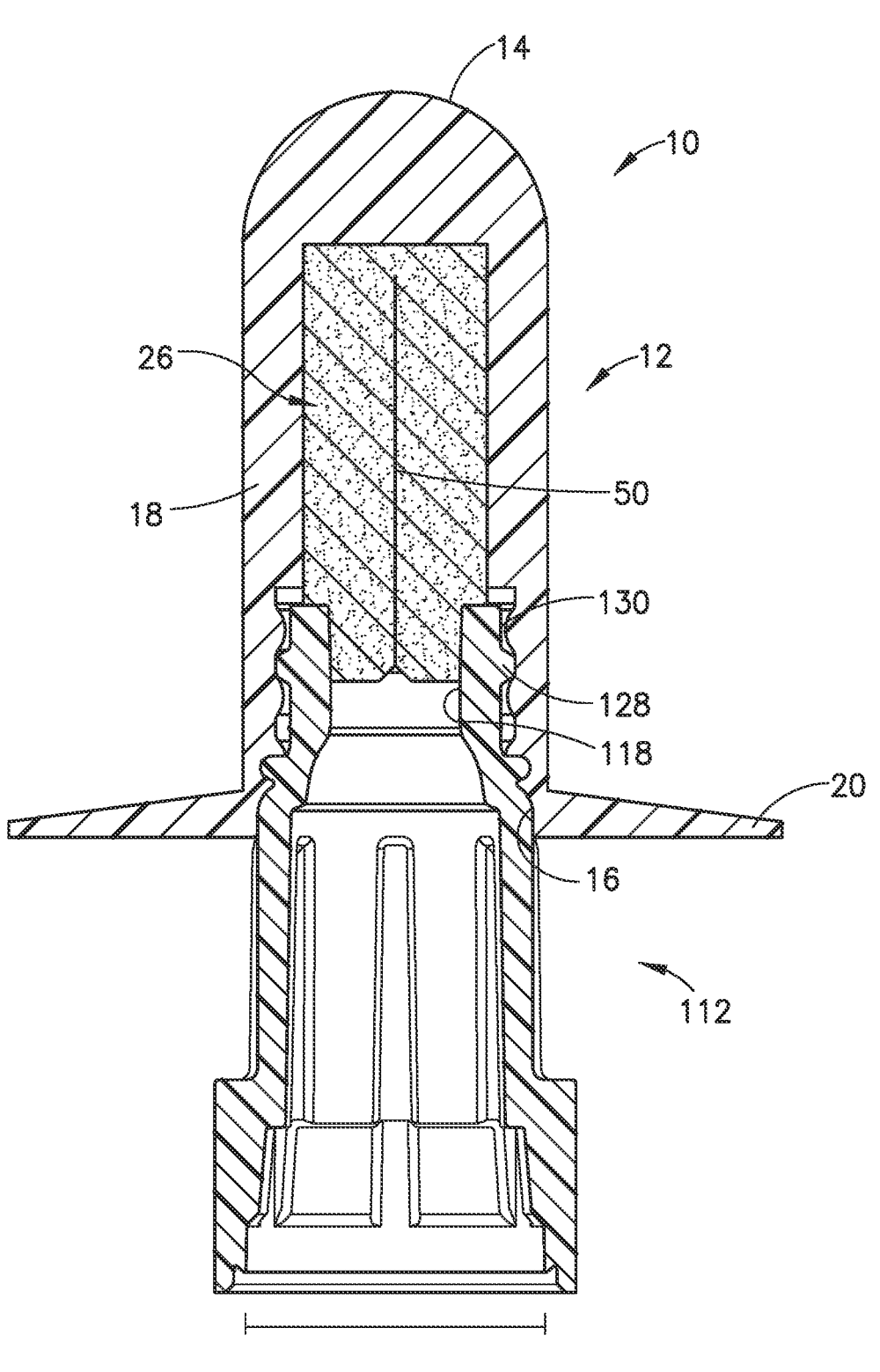
FIG. 3B is a cross-sectional view of the cap of FIG. 2A connected to the female needleless connector of FIG. 3A, according to an aspect of the present disclosure.
Figure 4:
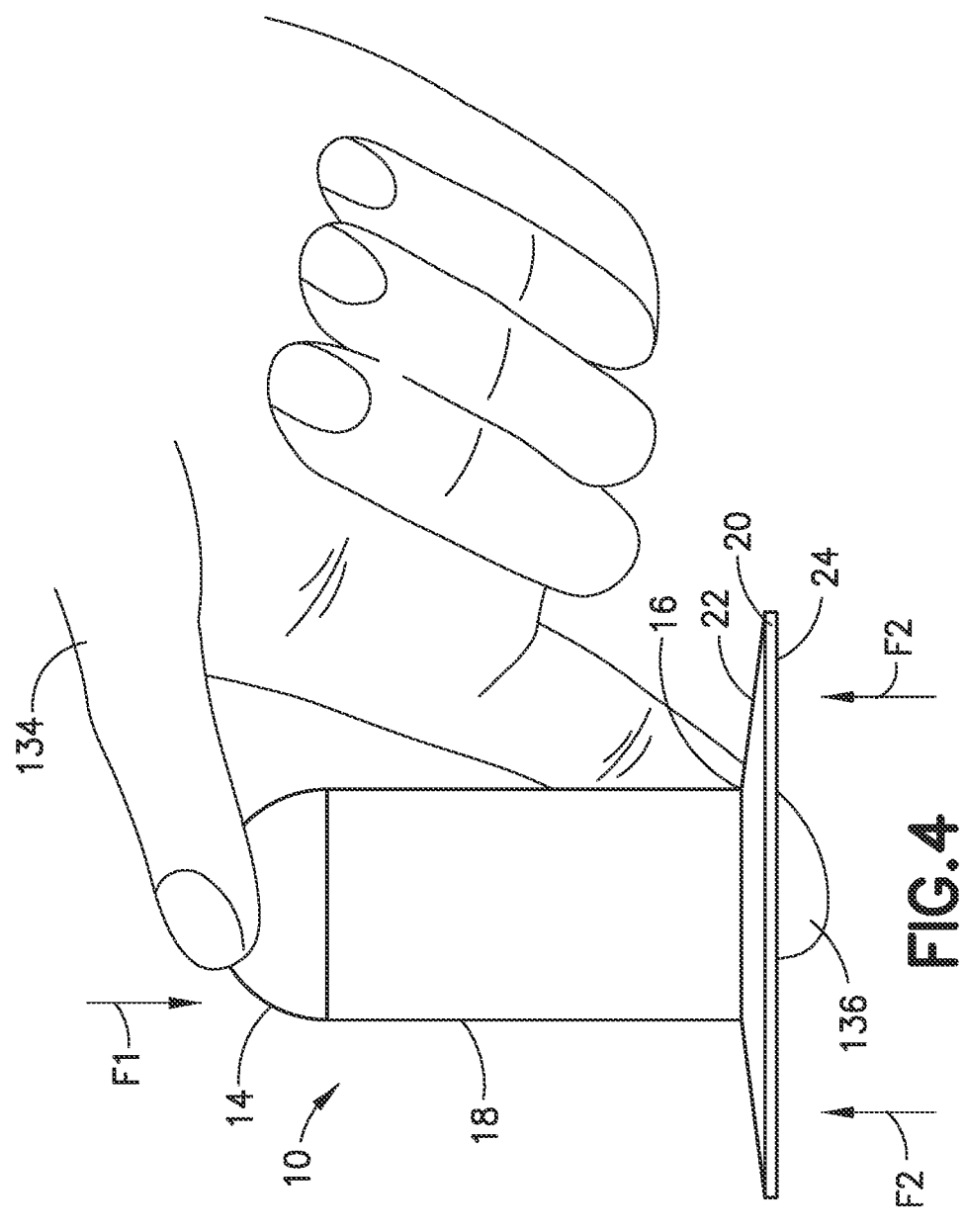
FIG. 4 is a schematic drawing showing a practitioner's hand positioned to move the cap from the initial position, suitable for engagement with a female connector, to a folded or retracted position, suitable for engagement with a male connector, according to an aspect of the present disclosure.

As previously described, the cap 10 of the present disclosure is a universal cap 10 configured to be connected to various types and sizes of male connectors 110 and female connectors 112. For example, FIGS. 3A and 3B show the cap 10 being connected to a female connector 112. FIG. 4 shows the cap 10 being moved from the initial position, suitable for connecting the cap 10 to the female connector 112, to the folded position, suitable for connecting the cap 10 to the male connector 110. FIGS. 6A-7B show the cap 10, in the folded position, being connected to a male connector 110.

In order to connect the cap 10 to a female connector 112, the practitioner first removes any packaging from the cap 10 and removes the protective cover 54 from the open bottom end 16 of the housing 12. Once the packaging and protective cover 54 are removed, the practitioner moves the female connector 112 towards the open bottom end 16 of the housing 12. For example, for a female connector 112, the practitioner moves the female connector 112 toward the housing 12 causing the septum 118 of the female connector 112 to contact the absorbent member 26. As previously described, contact between abrasive surfaces of the absorbent member 26 and surfaces of the female connector 112 can mechanically remove particles, such as microbes and other debris, from surfaces of the female connector 112, which contributes to the cleaning effect provided by the cap 10.

Continuing to move the female connector 112 into the housing 12 can bring outer surfaces 130 and threads 128 of the tubular distal portion 108 of the female connector 112 into contact with the absorbent member 26. Also, the continued movement of the female connector 112 into the housing 12 axially compresses the absorbent member 26 releasing the cleaning and/or disinfecting solution into the interior of the housing 12. As previously described, the released cleaning and/or disinfecting solution contacts, cleans, and disinfects portions of the female connector 112 including the septum 118, as well as outer surfaces 130 and threads 128 of the tubular distal portion 108 of the female connector 112.

In order to remove the cap 10 from the female connector 112, the practitioner grasps the sidewall 18 and/or flange 20 of the cap 10 and pulls the cap 10 axially away from the female connector 112. Beneficially, as previously described, the housing 12 does not include threads. Therefore, the practitioner does not need to twist or rotate the female connector 112 relative to the cap 10 to remove the female connector 112 from the cap 10. Instead, the practitioner need only pull the female connector 112 axially away from the cap 10 to remove the cap 10. Once removed, the cap 10 can be discarded, as it is often a single use product.

Once the female connector 112 is fully removed from the housing 12, the female connector 112 can be connected to a VAD. For example, the female connector 112 can be attached or inserted into a hub, port, or valve of the VAD forming a needleless fluid-tight connection between the female connector 112 and a fluid path, channel, or lumen of the VAD.

As previously described, the universal cap 10 can also be connected to a male connector 110, as shown in FIGS. 6A-7B. In order to connect the cap 10 to the male connector 110, the practitioner must first move the housing 12 of the cap 10 from the initial position (shown in FIGS. 2A-2C) to the folded position (shown in FIGS. 5A-5C). In order to move the cap 10 to the folded position, as shown in FIG. 4, the practitioner grasps the cap 10 and presses on the cap 10 and/or flange 20 causing the sidewall 18 to fold along the fold line or notch 40 to the folded position. For example, as shown in FIG. 4, the practitioner can press against the top end 14 of the housing 12 with a thumb 134 with a downwardly directed pressing force F1. The practitioner also presses against the downwardly facing surface 24 of the flange 20 with fingers (e.g., with an index finger 136) providing an upwardly directed force F2 against the flange 20. The combined downward force F1 and upward force F2 causes the sidewall 18 to flip or fold over, thereby moving the housing 12 of the cap 10 to the folded position.

Once the cap 10 is in the folded position, as shown in FIGS. 6A-7B, the cap 10 can be connected to the male connector 110. Specifically, in order to connect the cap 10 to the male connector 110, the practitioner moves the cap 10 towards the male connector 110 causing the lower portion 52 of the absorbent support 26 to contact the stem 114 of the male connector 110. Continuing to move the male connector 110 into the cap 10 causes the stem 114 to insert into the slit 50 of the absorbent member 26. Once inserted into the slit 50, inner surfaces of the absorbent member 26 contact outer surfaces of the stem 114 for scrubbing or mechanically removing particles, dirt, dust, microbes, and other debris from the outer surface of the stem 114. Continuing to move the male connector 110 into or toward the cap 10 next inserts the sidewall 18 of the cap 10 into the annular shield 122 of the male connector 110. As previously described, when the cap 10 is inserted into the annular shield 122, the outwardly facing surface of the folded over sidewall 18 of the housing 12 contacts the inner surface 126 and/or threads 124 of the annular shield 122 forming a friction engagement for connecting the cap 10 to the male connector 110. Also, cleaning and/or disinfecting solution released from the absorbent member 26 can contact the inner surface 126 and threads 124 of the annular shield 122 for cleaning and disinfecting these surfaces.

The cap 10 can be removed from the male connector 110 in a similar manner to how the cap 10 is removed from the female connector 112. For example, the practitioner can grasp the annular shield 122 of the male connector 110 in one hand and the sidewall 18 and/or flange 20 of the cap 10 in the other hand. The practitioner then moves the cap 10 axially away from the male connector 110, thereby releasing the cap 10 from the male connector 110. Once the cap 10 is released from the male connector 110, the cap 10 can be discarded and the male connector 110 can be attached to the port or hub of the VAD, as previously described.

While examples of the universal caps 10 and methods of use of the present disclosure are shown in the accompanying figures and described hereinabove in detail, other examples will be apparent to, and readily made by, those skilled in the art without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. A cap configured to engage at least a first connector and a second connector of different types, the cap comprising:
   a housing comprising a first end, an open second end, at least one sidewall
   extending between the first end and the second end, and a radially extending flange extending outward from the at least one sidewall or the open second end; and
   an absorbent member disposed in the housing configured to contain a cleaning solution for cleaning and/or disinfecting portions of the first connector or the second connector engaged to the cap,
   wherein the housing is configured to move between a first position, in which the housing is configured to engage the first connector, and a second position, in which the housing is configured to engage the second connector, by folding over the at least one sidewall of the housing such that, in the second position, the flange surrounds a portion of the at least one sidewall between the first end and the second end of the housing.

2. The cap of claim 1, wherein the first connector comprises a female luer connector, comprising:
   a tubular body defining a tapered cavity sized to receive a stem of a male luer connector;
   a septum over an opening of the tubular body; and
   an external thread extending radially outward from an outer surface of the tubular body,
   wherein the cap is engaged to the female connector by an interference or friction engagement between an inner surface of the at least one sidewall and the outer surface of the tubular body and/or the external thread of the female connector.

3. The cap of claim 1, wherein the second connector comprises a male luer connector, comprising:
   a stem comprising a proximal end, a distal end, and a tapered outer surface extending therebetween, the stem defining a fluid channel extending through the stem;

an annular shield about the stem connected to the proximal end of the stem; and a thread extending inward from an inner surface of the annular shield;

wherein the cap is engaged to the male connector by an interference or friction engagement between a portion of the at least one folded over sidewall and the inner surface of the annular shield of the male luer connector.

4. The cap of claim 1, wherein the first end of the housing comprises a dome-shaped outer surface and a substantially flat inner surface.

5. The cap of claim 1, wherein, in the second position, an outer surface of a lower portion of the at least one sidewall faces an outer surface of an upper portion of the at least one sidewall.

6. The cap of claim 5, wherein the at least one sidewall comprises a notch or groove in the at least one sidewall between the upper portion and the lower portion for facilitating folding over of the at least one sidewall to move the housing from the first position to the second position.

7. The cap of claim 5, wherein the housing further comprises a plurality of annular ridges comprising O-rings extending radially inward from an inner surface of the lower portion of the at least one sidewall.

8. The cap of claim 5, wherein a wall thickness of the lower portion of the at least one sidewall is less than a wall thickness of the upper portion of the at least one sidewall.

9. The cap of claim 1, wherein insertion of the first connector or the second connector into the housing causes the absorbent member to axially compress.

10. The cap of claim 9, wherein the axial compression of the absorbent member causes the cleaning solution of the absorbent member to contact threads and surfaces of the first connector or the second connector.

11. The cap of claim 1, wherein the absorbent member comprises a cylindrical body having an outer diameter that substantially matches a minimum inner diameter of the housing, and a slit extending axially through the cylindrical body.

12. The cap of claim 11, wherein the slit extends axially though the cylindrical body to a distal end of the cylindrical body.

13. The cap of claim 12, wherein portions of the cylindrical body separated by the slit are configured to separate to receive a stem of a male luer connector.

14. The cap of claim 1, wherein, with the housing in the first position, the absorbent member is enclosed within the housing and is accessible through the second open end of the housing, and, with the cap in the second position, a lower portion of the absorbent member protrudes beyond the at least one folded over sidewall of the housing.

15. The cap of claim 1, further comprising the cleaning solution absorbed by the absorbent member, the cleaning solution comprising Isopropyl Alcohol (IPA) and/or chlorhexidine gluconate.

16. The cap of claim 1, wherein the housing is moved from the first position to the second position by applying a downwardly directed force to the first end of the housing and/or applying an upwardly directed force to a distal surface of the flange.

17. A method for configuring the housing of the cap of claim 1 to engage the second connector of claim 1, the method comprising:

folding over the at least one sidewall of the cap, such that the housing moves from the first position to the second position; and inserting the second connector into the folded over cap, such that a stem of the second connector is received within a slit extending axially through the absorbent member.

18. The method of claim 17, wherein the second connector further comprising:

the stem comprising a proximal end, a distal end, and a tapered outer surface extending therebetween, the stem defining a fluid channel extending through the stem;

an annular shield about the stem connected to the proximal end of the stem; and a thread extending inward from an inner surface of the annular shield, wherein an inner diameter defined by the threads of the annular shield is less than a maximum outer diameter of the housing, when the housing is in the second position.

19. A method for configuring the housing of the cap of claim 1 to engage the first connector of claim 1, the method comprising inserting an end of the first connector into the cap, with the housing in the first position, such that a tubular body and/or other threads of the female connector contact the absorbent member.

20. The method of claim 19, wherein an outer diameter of the tubular body of the first connector is greater than a maximum inner diameter of the housing.

* * * * *